(12) United States Patent
Kraus et al.

(10) Patent No.: US 7,183,432 B2
(45) Date of Patent: Feb. 27, 2007

(54) SYNTHESIS OF YNAMIDES

(75) Inventors: George A. Kraus, Ames, IA (US); Jaehoon Bae, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 141 days.

(21) Appl. No.: 11/092,333

(22) Filed: Mar. 29, 2005

(65) Prior Publication Data

US 2005/0272954 A1    Dec. 8, 2005

Related U.S. Application Data

(60) Provisional application No. 60/577,125, filed on Jun. 4, 2004.

(51) Int. Cl.
*C07C 233/09* (2006.01)

(52) U.S. Cl. ................. 564/204; 564/205; 554/35; 554/68

(58) Field of Classification Search ............... 564/204, 564/205; 554/35, 68
See application file for complete search history.

(56) References Cited

OTHER PUBLICATIONS

Molgaard et al, J. Agric. Food chem., 2003, 51, 6922-6933.*
Wu et al, Phytochemistry, 65 (2004) 2477-2484.*
Kraus et al, Tetrahedron Letters, 44 (2003) 5505-5506.*
Kraus, George A., et al. "Synthesis of *N*-(2-methylpropyl)-2E-undecene-8, 10-dlynamide, a novel constituent of *Enchinacea angustifolia*" Tetrahedron Letters 44, 2003 Elsevier Science Ltd.

* cited by examiner

*Primary Examiner*—Shailendra Kumar
(74) *Attorney, Agent, or Firm*—McKee, Voorhees & Sease, P.L.C.

(57) ABSTRACT

A method of synthesizing diacetylenic amides is described. The key steps of the invention include the reaction of an aldehyde with the monoanion of a diacetylene and the reductive removal of a propargylic alcohol. The invention offers the first known method of synthesizing diacetylenic amides that are naturally isolated from *Echinacea* through a direct and flexible route.

18 Claims, No Drawings

SYNTHESIS OF YNAMIDES

CROSS-REFERENCE TO RELATED APPLICATIONS

This application claims priority to U.S. Provisional Patent Applications Ser. No. 60/577,125 filed Jun. 4, 2004, which is incorporated by reference herein in its entirety.

GRANT REFERENCE CLAUSE

This invention was funded in part by N.I.H. Contract No. ES012020. The government may have certain rights in this invention.

FIELD OF THE INVENTION

This invention relates to methods of synthesizing ynamides which are diacetylenic amides. Specifically, this invention relates to methods of synthesizing ynamides found in unisolated form in the herb *Echinacea angustifolia*, including N-(2-methylpropyl)-2E-undecene-8,10-diynamide, and relates to methods of their use and manufacture.

BACKGROUND OF THE INVENTION

*Echinacea* is a native plant of North America and traditionally is used to combat cold, flu, cough, sore throats and many other ailments. Today, *Echinacea* is among the most frequently utilized medicinal herbs around the world for use in supplements and personal care formulations. The consumption of *Echinacea* has significantly increased in Europe and North America, with a market share of about 10% of the herbal industry in the United States (Rawls 1996). In Russia, *E. purpurea* tops are mixed with animal feeds to improve the natural resistance of cattle to diseases, and improve milk production and quality. Numerous attempts have been underway in some non-traditional Echinacea growing countries, in Africa, Asia, Latin America, and the Middle East to introduce cultivation, processing, and marketing. Today, *E. purpurea* in the markets originates solely from cultivation, while *E. angustifolia, E. pallida, E. paradoxa, E. tenneseensis*, and *E. sanguinea* raw materials are sourced either from partial cultivation or totally collected from the wild.

Among the many novel natural products isolated from *E. angustifolia* are a series of diacetylenic amides. A complex mixture containing at least twelve different acetylenic amides can be obtained by supercritical fluid extraction of fresh dried *E. angustifolia* roots. In addition to its properties described above, these amides have been shown to be active against the larvae of mosquito species *Aedes aegypti*. These amides have also been found to be active against neonates of the corn bollworm *Helicoverpa zea*.

Investigations of the pharmacological and biological activities of purported *Echinacea* extracts have frequently shown them to be of widely differing character. With the evolution of botanical products, there has been an increasing demand for *Echinacea* having consistent and defined pharmacological properties. While it would be advantageous to artificially synthesize *Echinacea* extracts in order to achieve better consistency, to date such attempts have been unsuccessful.

Accordingly, it is a primary objective of the present invention to provide a method and means of synthesizing ynamides.

It is a further objective of the present invention to provide a method and means of synthesizing diacetylenic amides.

It is a further objective of the present invention to provide a method and means of synthesizing diacetylenic amides that provides for economical, easy, and high yield processing.

It is a further objective of the present invention to provide a method and means of synthesizing pure diacetylenic amides that are natural constituents of *Echinacea* extracts.

It is still a further objective of the present invention to provide a method and means of synthesizing pure form diacetylenic amides that are present as natural constituents of *Echinacea angustifolia*, but in mixtures.

It is yet a further objective of the present invention to provide a method and means of synthesizing N-(2-methylpropyl)-2E-undecene-8,10-diynamide.

The method and means of accomplishing each of the above objectives as well as others will become apparent from the detailed description of the invention which follows hereafter.

SUMMARY OF THE INVENTION

The invention describes a method and means of synthesizing in pure form diacetylenic amides, many of which are naturally present in *Echinacea*. These compounds have the general formula:

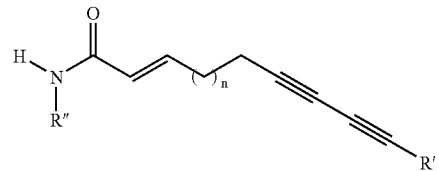

wherein R' is a functionalized chain that is stable in pH ranging from about 8–12, R" is a branched alkyl chain, and n is an integer equal to the number of carbons minus four in the alcohol starting material for synthesizing the compounds of this invention. The alkene can have either the E- or Z-configuration.

The diacetylenic amides are synthesized by first reacting an alcohol starting material with a reagent that is functionally capable of isomerizing the alcohol into a terminal acetylene (i.e., KAPA reagent). The terminal acetylene is next reacted with a halogen, followed by reaction with a second acetylene for a time period sufficient to form a diacetylenic alcohol. This alcohol is oxidized, then reacted with a Wittig reagent to form the diacetylenic amides of the invention.

DETAILED DESCRIPTION OF THE PREFERRED EMBODIMENT

The present invention relates to the synthesis in high yield and pure form of a subclass of ynamides, diacetylenic amides, many of which exist in mixture in *Echinacea*. The diacetylenic amides of this invention have the following general structural formula:

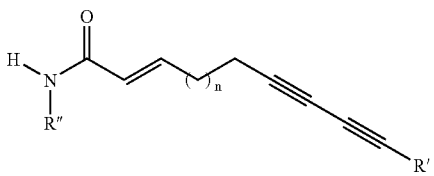

wherein R' is a functionalized chain that is stable in pH ranging from about 8–12, R" is a branched alkyl chain, and n is an integer equal to the number of carbons minus four in the alcohol starting material for synthesizing the compounds of this invention.

Preferably, R' is selected from the group consisting of non-functionally substituted alkyl, alcohol, ketal, alkenyl, alkynyl, and ether. Most preferably, R' is selected from the group consisting of a $C_1$–$C_{12}$ alkyl, alcohol, ketal, alkenyl, alkynyl, and ether.

Preferably, R" is a non-functionally substituted $C_1$–$C_{12}$ branched alkyl chain, that is most preferably isobutyl, isopentyl, or isopropyl.

In accordance with the first step of the process of this invention, a propargyl alcohol of the following formula is the starting material:

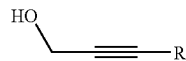

wherein R is a non-functionally substituted unbranched alkyl chain, which is preferably $C_1$–$C_{25}$, and most preferably $C_1$–$C_{12}$. The R moiety must be non-functionally substituted in order to prevent undesired side reactions from occurring on this side chain moiety.

The alcohol starting material is reacted with a material that is functionally capable of moving the acetylene to the end of the chain. Such materials are well known in the art. A preferred compound for this purpose is KAPA reagent (potassium 3-aminopropyl amide). Persons skilled in the art can readily determine other reagents that are suitable for this purpose. The alcohol is reacted with the KAPA or other suitable reagent for a time period sufficient for this chemical shift to occur, which will generally range from about 1–2 hours. The KAPA (or other reagent) should be combined with the alcohol starting material in a ratio of greater than 1:1 reagent to alcohol. Preferably this addition occurs at an elevated temperature of, for example, 70° C. with stirring.

The resulting terminal acetylene is next reacted with a halogen that is either iodine or bromine for a time period sufficient to add a terminal halide group to the acetylene. The terminal acetylene should be combined with the iodine or bromine in a ratio of greater than 1:1 iodine/bromine to acetylene. This reaction is shown in the examples may occur in the presence of base such as potassium hydroxide, methyl alcohol and water. Temperature is not critical, but it may start at 0° C., and warm to room temperature with stirring over a two hour time.

The halogenated acetylene is next coupled with a second acetylene for a time period sufficient to form the new carbon-carbon bond. The second acetylene has the general formula HCCR' wherein R' has the same meaning as already described above. There is no criticality with regard to the acetylene compound used in this respect, with its precise structure depending upon the structure of the diacetylenic amide desired. Generally, however, both substituted and unsubstituted, straight chain, branched chain and cyclic compounds may be used as well as aromatics, both substituted and unsubstituted. Examples of appropriate R' groups include, but are not limited to, disulphides, alkylhalides, aldehydes, ketones, esters, silanes, and epoxides. One example of an appropriate acetylene for this purpose is trimethylsilylacetylene. The ratio of halogenated acetylene to second acetylene is preferably 1:1. A palladium catalyst is necessary.

If a TMS-substituted acetylene is used as the acetylene in the coupling reaction, the silyl group may be removed if desired by reaction of the diacetylene with fluoride.

The resulting alcohol is next oxidized to produce the aldehyde. Any oxidation method may be used in this respect. Methods of oxidizing alcohols are well known in the art and include, but are not limited to, Swern oxidation, K. Omura, D. Swern, *Tetrahedron* 34, 1651 (1978), pyridinium chlorochromate (PCC) oxidation. Swern oxidation is promoted by oxalyl chloride activation of DMSO (dimethyl sulfoxide). The aldehyde formed has the following general formula:

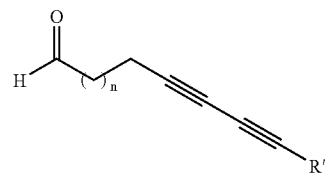

wherein R' and n have the same meanings as already described above.

The aldehyde then undergoes a Wittig reaction to form an unsaturated amide. The Wittig reaction is well known in the art, and involves alkene formation from carbonyl compounds and phosphonium ylides (Wittig reagents), proceeding primarily through the proposed betaine and/or oxaphosphetane intermediates.

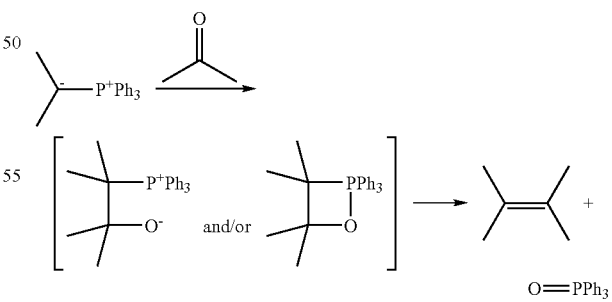

Wittig reagents for use in the invention have the general formula $Ph_3PCHCONHR"$ whereby R" has the same meaning as set forth above. Examples of appropriate Wittig reagents for this reaction include, $Ph_3PCHCONHiBu$. The ratio of Wittig reagent to aldehyde is preferably 1:1

The final products of this reaction scheme are diacetylenic amides having the following general formula:

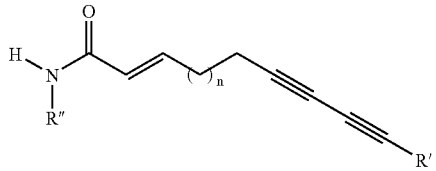

wherein R', R", and n have the same meanings as already described above. The alkene can have either the E- or Z-configuration.

Temperatures for the reactions described above have not been found to be critical, although it has been found desirable to react at room temperature or lower. Pressure does not appear to be a controlling factor. Atmospheric pressure works satisfactorily. The reactions are preferably employed in an inert atmosphere.

The following examples are offered to illustrate but not limit the invention. Thus, they are presented with the understanding that various formulation modifications as well as method of delivery modifications may be made and still be within the spirit of the invention.

EXAMPLE

Preparation of Diacetylenic Amide (E-N-isobutyl undeca-2-ene-8,10-diynamide)

A diacetylenic amide from *Echinacea* was synthesized in accordance with the methods of this invention.

The compound had the following general structure:

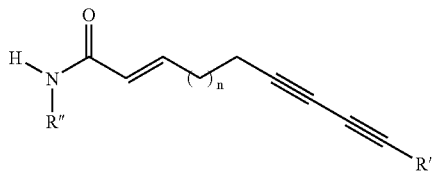

whereby R" is isobutyl, n is 3 and R' is H.

The synthesis scheme is set forth below:

Strategy Accomplished in Laboratory

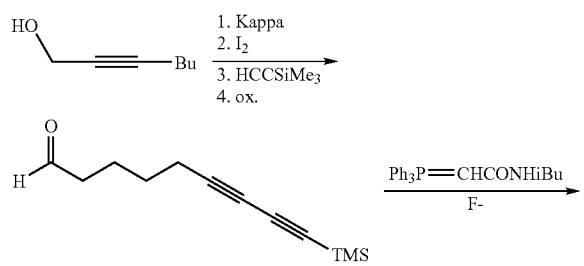

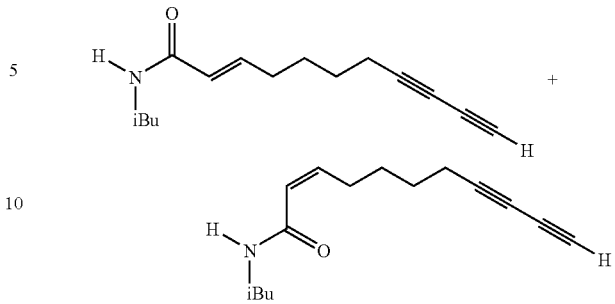

Starting from commercially available heptynol, the KAPA reagent was used to move the acetylene to the end of the chain. The resulting terminal acetylene was converted into the iodoacetylene using iodine and then coupled with trimethylsilylacetylene (TMS). The primary alcohol was oxidized to the aldehyde. This aldehyde was treated with a Wittig reagent, followed by desilylation with fluoride to provide the acetylenic amides from *Echinacea*, specifically the following occurred.

6-pentyn-1-ol

To 10 ml of 1,3-diaminopropane was added lithium metal (186 mg, 27 mmol) in argon atmosphere. After stirring for 2 hrs at 70° C., solution was cooled to rt. To a mixture was added t-BuOK (1.69 g). After 15 min of stirring, 2-heptynol (0.507 ml, 4 mmol) was added to a mixture then stirred for 1 hr at rt. Reaction was quenched by adding 20 ml of water, extracted with ether (30 ml three times), washed with 10% HCl solution, and dried over $MgSO_4$. Solvent was removed—74% yield.

7-iodo-6-pentyn-1-ol

To a solution of 6-heptynol (331 mg, 2.95 mmol) in 10 ml of methanol was added KOH in 5 ml of $H_2O$. After 10 min, iodine (824 mg, 3.24 mmol) was added at 0° C. and warmed to rt and stirred for 2 hr. The reaction was then quenched with water and extracted with ether (20 ml three times). The solvent was removed in vacuo, the residue dissolved in $CH_2Cl_2$, washed with brine and dried over $MgSO_4$. Purification by silica gel chromatography (hexane:ethyl acetate=4:1) gave the product 498 mg (71% yield).

9-trimethylsilyl-6,8-nonadiyn-1-ol

To a solution of 7-iodo-6-heptynol (100 mg, 0.42 mmol), trimethylsilylacetylene (0.072 ml, 0.5 mmol), diphenyldichloropaladium (10 mg) and copper iodide (3 mg) in 5 ml of THF was added diisopropylamine (0.150 ml) at rt in argon atmosphere. After stirring 1 hr at rt, the mixture was diluted with ether, washed with $NH_4Cl$ solution, water and brine, dried over $MgSO_4$ and concentrated. Purification by silica gel chromatography (hexanes:ethyl acetate=4:1) gave 50 mg of product (50% yield).

2 5 9-trimethylsilyl-6,8-nonadiynaldehyde

To a solution of alcohol (50 mg, 0.24 mmol) in 2 ml of $CH_2Cl_2$ was added PCC (78 mg, 0.36 mmol) at rt. After 1 hr, 20 mg of PCC was added. After 30 min, reaction was quenched by adding ether and filtered through Celite, concentrated and purified by silica gel chromatography (hexanes:ethyl acetate=2:1) gave 46 mg of product (93% yield).

E-N-isobutyl undeca-2-ene-8,10-diynaniide and
Z-N-isobutyl undeca-2-ene-8,10-diynamide To a solution of N-isobutyl triphenylphosphonium acetamide (0.415 g, 1.01 mmol) in 3 ml of THF was added 2.5M n-BuLi in hexane (0.404 ml, 1.01 ml) at 0° C. After stirring for 10 min at 0° C., aldehyde (104 mg, 0.51 mmol) in THF was added dropwise at 0° C. After stirring for 30 min at 0° C., reaction was quenched with water. The solution was then extracted with ether and dried over $MgSO_4$. The residue was purified by silica gel chromatography (hexane:ethyl acetate=10:1) to give Z compound (15 mg, 10% yield) and E compound (112 mg, 73% yield).

To a solution of amide (0.029 g, 0.096 mmol) in THF (1 mL) was added 1M TBAF (0.144 mL, 0.144 mmol) at 0 ° C. After stirring for 30 min, the solvent was removed in vacuo. The residue was purified by silica gel chromatography (hexane:ethyl acetate=10:1) to give the product (0.021 g, 95% yield).

E-N-isobutyl undeca-2-ene-8,10-diynamide: 300 MHz $^1$H NMR ($CDCl_3$) 6.79 (1H, dt, J=15.3, 6.6 Hz), 5.79 (1H, d, J=15.3 Hz), 5.62 (1H, br), 3.13 (2H, t, J=6.6 Hz), 2.23~2.29 (2H, m), 2.16~2.22 (2H, m), 1.97 (1H, t, J=0.9 Hz) 1.74~1.83 (1H, m), 1.52~1.59 (4H, m), 0.91 (6H, d, J=6.9 Hz); $^{13}$C NMR 166.1, 143.8, 124.3, 78.1, 68.6, 65.2, 64.9, 47.1, 31.5, 28.8, 27.6, 27.5, 20.3, 19.0. HRMS (EIMS) m/z for $C_{15}H_{21}NO$ calcd 231.16231, measured 231.16260. EIMS 70 eV, m/z (rel. int.): 231 $[M]^+$ (6), 216 $[M-CH_3]^+$ (8), 202 (27), 188 $[M-C_3H_7]^+$ (22), 174 $[M-C_4H_9]^+$ (16), 160 (21), 131 $[M-C_5H_{10}NO]^+$ (43), 116 (56), 103 (40), 91 $[C_7H_7]^+$ (100), 55 (26), 41 (25).

Z-N-isobutyl undeca-2-ene-8,10-diynamide: 300 MHz $^1$H NMR ($CDCl_3$) 5.96 (1H, dt, J=11.4, 7.5 Hz), 5.69 (1H, d, J=11.4 Hz), 5.49 (1H, br), 3.11 (2H, t, J=6.9 Hz), 2.64~2.72 (2H, m), 2.57~2.30 (2H, m), 1.95 (1H, t, J=1.2 Hz), 1.72~1.86 (1H, m), 1.50~1.63 (4H, m), 0.92 (6H, d, J=6.6 Hz).; $^{13}$C NMR 166.6, 145.0, 122.9, 78.5, 68.7, 65.0, 64.7, 46.8, 28.8, 28.5, 28.2, 27.8, 20.4, 19.1. EIMS 70 eV, m/z (rel. int.): 231 $[M]^+$ (4), 216 $[M-CH_3]^+$ (5), 202 (14), 188 $[M-C_3H_7]^+$ (11), 174 $[M-C_4H_9]^+$ (12), 159 (18), 131 $[M-C_5H_{10}NO]^+$ (98), 117 (100), 91 $[C_7H_7]^+$ (82), 57 (57), 41 (48).

It should be appreciated that the compounds of this invention may contain ynamides within the scope of the formulas described above, or prodrugs or analogues of these compounds and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of preparing diacetylenic amides comprising: reacting an aldehyde starting material with a compound that isomerizes the aldehyde to form a terminal acetylene; reacting the terminal acetylene with a halogen for a time period sufficient to form a terminally halogenated acetylene; coupling a second acetylene to the halogenated acetylene to form a diacetylenic propargylic alcohol; oxidizing the propargylic alcohol to form a diacetylenic aldehyde; and reacting the diacetylenic aldehyde with a phosphonium ylide to form a diacetylenic amide.

2. The method of claim 1 whereby the aldehyde starting material has the following structure:

HO—CH$_2$—C≡C—R wherein R is a non-functionally substituted unbranched alkyl chain.

3. The method of claim 2 whereby the alkyl chain is $C_1$–$C_{25}$.

4. The method of claim 3 whereby the alkyl chain is $C_1$–$C_{12}$.

5. The method of claim 1 whereby the isomerizing compound is potassium 3-aminopropyl amide.

6. The method of claim 1 whereby the aldehyde is reacted with the isomerizing compound in a ratio of >1:1 isomerizing compound to aldehyde.

7. The method of claim 1 whereby the halogen is selected from the group consisting of iodine and bromine.

8. The method of claim 1 whereby the acetylene is reacted with the halogen in a ratio of >1:1 halogen to acetylene.

9. The method of claim 1 whereby the second acetylene has the general formula HCCR', whereby R' is selected from the group consisting of non-functionally substituted disulphides, alkylhalides, aldehydes, ketones, esters, silanes, and epoxides.

10. The method of claim 9 whereby the second acetylene is trimethylsilylacetylene.

11. The method of claim 1 whereby the alcohol is oxidized by a method selected from the group consisting of Swern oxidation, PCC oxidation.

12. The method of claim 1 whereby the alcohol is oxidized to form a diacetylenic aldehyde of the following general formula:

$$H-C(=O)-(CH_2)_n-C\equiv C-C\equiv C-R'$$

wherein $R_1$ is selected from the group consisting of non-functionally substituted alkyl, alcohol, ketal, alkenyl, alkynyl, and ether; and n is an integer equal to the number of carbons in the aldehyde starting material.

13. The method of claim 1 whereby the diacetylenic aldehyde is reacted with a phosphonium ylide $Ph_3PCHCONHiBu$.

14. The method of claim 1 whereby the diacetylenic amides formed have the following general formula:

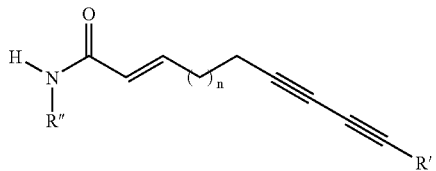

wherein R' is a functionalized chain that is stable in pH ranging from about 8–12, R" is a branched alkyl chain, and n is an integer equal to the number of carbons minus four in the alcohol starting material for synthesizing the compounds of this invention.

15. The method of claim 14 whereby R' is selected from the group consisting of non-functionally substituted alkyl, alcohol, ketal, alkenyl, alkynyl, and ether.

16. The method of claim 15 whereby R' is selected from the group consisting of a $C_1$–$C_{12}$ alkyl, alcohol, ketal, alkenyl, alkynyl, and ether.

17. The method of claim 16 whereby R" is a non-functionally substituted $C_1$–$C_{12}$ branched alkyl chain.

18. The method of claim 17 whereby R" is selected from the group consisting of isobutyl, isopentyl, and isopropyl.

* * * * *